US 11,449,462 B2

(12) United States Patent
Chen et al.

(10) Patent No.: US 11,449,462 B2
(45) Date of Patent: Sep. 20, 2022

(54) FLUID OPTICAL DATABASE RECONSTRUCTION METHODS AND APPLICATIONS THEREOF

(71) Applicant: Halliburton Energy Services, Inc., Houston, TX (US)

(72) Inventors: Dingding Chen, Tomball, TX (US); Bin Dai, Spring, TX (US); Christopher Michael Jones, Houston, TX (US); Jing Shen, Houston, TX (US); Anthony Van Zuilekom, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 810 days.

(21) Appl. No.: 16/347,243

(22) PCT Filed: Jul. 3, 2018

(86) PCT No.: PCT/US2018/040791
§ 371 (c)(1),
(2) Date: May 3, 2019

(87) PCT Pub. No.: WO2020/009696
PCT Pub. Date: Jan. 9, 2020

(65) Prior Publication Data
US 2020/0257654 A1 Aug. 13, 2020

(51) Int. Cl.
*G01N 21/3577* (2014.01)
*G01N 21/94* (2006.01)
(Continued)

(52) U.S. Cl.
CPC ............ *G06F 16/122* (2019.01); *E21B 49/08* (2013.01); *G01N 21/3577* (2013.01);
(Continued)

(58) Field of Classification Search
CPC .... E21B 49/08; G01N 21/3577; G01N 21/94; G01N 33/2823; G01N 2201/12; G01V 8/10; G06N 3/0454; G06N 3/08
See application file for complete search history.

(56) References Cited

U.S. PATENT DOCUMENTS

| 6,178,815 B1 * | 1/2001 | Felling .................... E21B 49/10 73/152.19 |
| 6,343,507 B1 * | 2/2002 | Felling .................... E21B 49/10 175/5 |

(Continued)

FOREIGN PATENT DOCUMENTS

| WO | 2016093853 A1 | 6/2016 |
| WO | 2016137472 A1 | 9/2016 |

(Continued)

OTHER PUBLICATIONS

PCT Application Serial No. PCT/US2018/040791, International Search Report, dated Mar. 27, 2019, 3 pages.
(Continued)

*Primary Examiner* — David P Porta
*Assistant Examiner* — Fani Polyzos Boosalis
(74) *Attorney, Agent, or Firm* — Delizio, Peacock, Lewin & Guerra

(57) ABSTRACT

Mutual-complementary modeling and testing methods are disclosed that can enable validated mapping from external oil and gas information sources to existing fluid optical databases through the use of forward and inverse neural networks. The forward neural networks use fluid compositional inputs to produce fluid principal spectroscopy components (PSC). The inverse neural networks apply PSC inputs to estimate fluid compositional outputs. The fluid compositional data from external sources can be tested through forward models first. The produced PSC outputs are then entered as inputs to inverse models to generate fluid compositional data. The degree of matching between reconstructed fluid compositions and the original testing data suggests which part of the new data can be integrated directly into the existing database as validated mapping. The applications of using PSC inputs to reconstruct infrared
(Continued)

spectra and estimate oil-based-mud (OBM) contamination with endmember spectral fingerprints are also included.

20 Claims, 9 Drawing Sheets

(51) Int. Cl.

| | | |
|---|---|---|
| *G01V 8/10* | (2006.01) | |
| *G06N 3/08* | (2006.01) | |
| *G06F 16/11* | (2019.01) | |
| *E21B 49/08* | (2006.01) | |
| *G01N 33/28* | (2006.01) | |
| *G06N 3/04* | (2006.01) | |

(52) U.S. Cl.
CPC ......... *G01N 21/94* (2013.01); *G01N 33/2823* (2013.01); *G01V 8/10* (2013.01); *G06N 3/0454* (2013.01); *G06N 3/08* (2013.01); *G01N 2201/12* (2013.01)

(56) References Cited

U.S. PATENT DOCUMENTS

| | | |
|---|---|---|
| 10,436,028 B2 | 10/2019 | Dai et al. |
| 10,641,091 B2 | 5/2020 | Chen et al. |
| 2015/0292324 A1 | 10/2015 | Jackson et al. |
| 2016/0177715 A1 | 6/2016 | Indo et al. |

FOREIGN PATENT DOCUMENTS

| | | |
|---|---|---|
| WO | 2018084852 A1 | 5/2018 |
| WO | 2018084853 A1 | 5/2018 |
| WO | 2018144606 A1 | 8/2018 |
| WO | 2020005238 A1 | 1/2020 |

OTHER PUBLICATIONS

PCT Application Serial No. PCT/US2018/040791, International Written Opinion, dated Mar. 27, 2019, 5 pages.

\* cited by examiner

FLUID OPTICAL DATABASE RECONSTRUCTION METHODS AND APPLICATIONS THEREOF

TECHNICAL FIELD

The present description relates in general to fluid optical database reconstruction methods, and more particularly to, for example, without limitation, fluid optical database reconstruction by integrating large number of fluid samples with diverse compositions and properties from external sources and recovering incomplete data through validated modeling and testing, and applications thereof.

BACKGROUND

In the field of oil and gas exploration and production, characterization of formation or wellbore fluid compositions and properties is important for reservoir fluid evaluation. For example, reservoir fluid evaluation deploys formation sampling and testing techniques to collect fluid samples with minimized contamination and compare with data from existing databases to further facilitate early decision making on the economic value of potential reservoir exploration, well completion and production based on the quality prediction of the fluid compositions and properties. For example, data bases, such as a fluid optical database is defined as a database containing fundamental information needed in surface optical fluid analysis and downhole formation sampling and testing.

The database is often limited by the number of fluid samples, particularly live oils, sample geological distribution over different field origins, and fluid types and compositions that represent typical reservoir fluids encountered during global formation sampling and testing. Expanding the database through laboratory experiments alone is slow and cost-prohibitive. External databases, e.g., publically available databases, however, can include large amounts of fluids with diverse compositions; however, these are often incomplete or inconsistent with respect to all properties and can entirely miss fluid optical data. Furthermore, the measurements from various laboratories or data acquisition systems are often gathered with inconsistent methodologies and may contain ill-posed problems that induce additional complexity for system identification. Because of these combined issues, improving the usefulness of the database may be challenging. Therefore, new and novel database improvement methods are urgently needed.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 1A illustrates a schematic view of a logging operation deployed in and around a wellbore system and FIG. 1B illustrates a schematic view of a wireline logging operation deployed in and around a wellbore system.

Figure 1A:
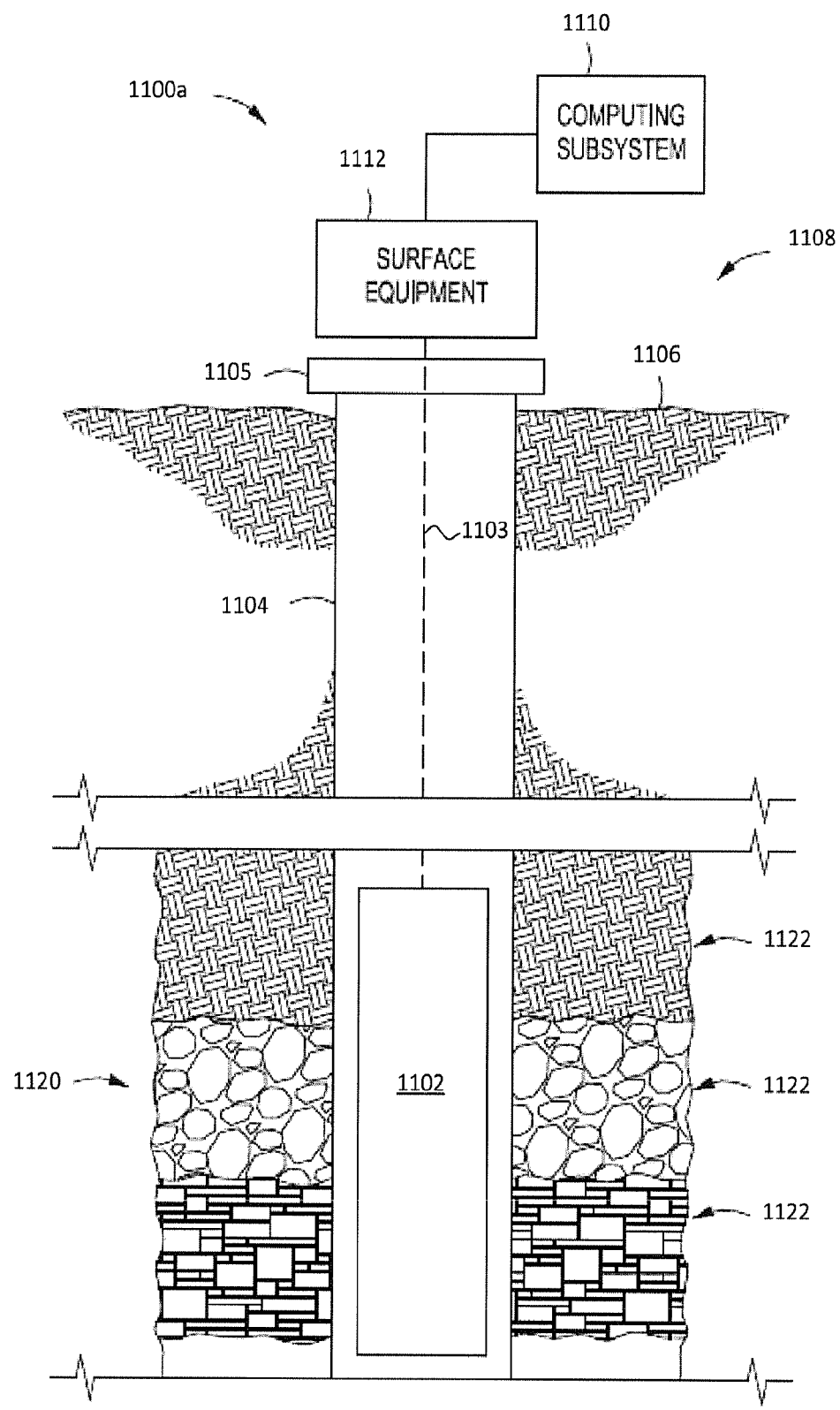
FIGS. 1A and 1B illustrate wellbore systems.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

A fluid optical database, which contains fundamental information needed in surface optical fluid analysis and downhole formation sampling and testing, is essential for optical sensor/tool design optimization, fluid answer product calibration and validation, sensor/tool prediction uncertainty evaluation, and fluid sampling contamination analysis. A typical existing fluid optical database, for example, might have wide-range fluid optical spectral data measured at standard pressure, volume, and temperature (PVT) conditions with particular types of spectrometers and fluid compositional and property data obtained from practical gas chromatography (GC) analysis. As stated above, an improved or a more complete fluid optical database can be used, e.g., in designing, optimizing, fabricating and/or manufacturing of a multivariate optical element (MOE) or integrated computation element (ICE). Using the improved database, a user can calibrate an optical sensor tool, e.g. by updating the calibration file used in a downhole tool. In some cases, the improved database may reduce uncertainty in the calibration or measurement data. Reducing uncertainty can improve confidence of the measured data or calibration efforts of the downhole tool. In some cases, reduced uncertainty may obviate the need for post processing, thereby allowing a faster deliverable to the user. In some implementations, real-time prediction can be afforded at the job site if the uncertainty is reduced to a level low enough to mitigate certain assumptions. In some implementations, the improved database can enable better predictions of contamination in and around a wellbore site, which in turn can reduce pump out time, thereby reducing rig time and saving money. This is when a downhole tool sensor is used in conjunction with an improved database to determine optimum pump-out time.

The advanced formation sampling and testing with downhole optical tools in today's application, for example, requires state-of-the-art modeling with fluid compositions, spectroscopies, and operational sensors data. Current data mining and machine learning technology make modeling analytics robust and efficient, and demand leveraged databases in both data diversity and consistency. However, an internal fluid optical database is often limited by the number of fluid samples, especially live oils, the sample geological distribution, and the fluid types and compositions that represent typical reservoir fluids encountered in global formation sampling and testing. The internal fluid database refers to a limited or privately owned database. In some embodiments, the internal fluid database refers to a database that resides on a downhole tool. External databases, on the other hand, may include large number fluids with diverse compositions and properties, but often miss optical measurement data. An external database refers to a publically available database. The construction of a large fluid optical database with complete measurement data through conventional methods alone is expensive. The measurement data obtained from various laboratories or data acquisition systems may also contain ill-posed problems that induce added complexity for system identification. Because of these combined issues, improving the cost-effectiveness of database reconstruction can include, among other factors, leveraging a larger and complete database from the internal and external sources, incorporating the simulated data into the merged structure that lacks measurement data, and validating data integration through advanced machine learning and testing procedures.

The subject disclosure presents a mutual-complementary modeling and testing method that enables validated mapping from external oil and gas information sources to an existing fluid optical database through the use of forward and inverse neural networks. The forward neural networks use fluid compositional inputs to produce fluid principal spectroscopy components (PSC). The inverse neural networks apply PSC inputs to estimate fluid compositional outputs. The fluid compositional data from external sources can be tested through forward models first. The produced PSC outputs are then entered as inputs to inverse models to generate fluid compositional data. The degree of matching between reconstructed fluid compositions and the original testing data suggests which part of the new data can be integrated directly into the existing database as validated mapping. It also indicates the degree of additional effort needed to overcome the limitation of current forward and inverse models and to improve future applicability. In practice, these models are used in conjunction with other optical sensor signal standardization/transformation and fluid spectra deconvolution neural networks to reconstruct an extended fluid optical database with improved cost-effectiveness.

In one or more embodiments, fluid PSC data can be estimated using known fluid composition inputs with forward neural network predictive models. This implementation can be sensor independent, making quality data mapping from fluid compositional inputs to generic and full-range parameterized PSC outputs powerful. One or more other embodiments include a model validating method to evaluate the uncertainty of simulation results on PSC by comparing the consistency of inversion estimated fluid compositional data driven by PSC inputs with corresponding target fluid data available from external sources. One or more other embodiments include a fluid spectral reconstruction method employing a full-range PSC estimation produced by statistics of a neural network ensemble. The spectral re-construction method can be implemented with a visible (VIS), near infrared (NIR) and mid infrared (MIR) spectral deconvolution algorithm respectively using neural networks for cost-effective commercialization.

In some embodiments, a method is provided to optimize optical sensor data to PSC data transformation once field job results from an external source (lab results from the third party, for example) become available. After the estimated PSC data are validated by applying forward and inverse neural network models as discussed above, they can be integrated as target outputs of additional reference fluids to update sensor to PSC data transformation, providing improved robustness.

As described above, feasibility studies are conducted on field data and additional oil and gas information sources exemplify the application of using mutual-complementing and other neural networks for optical tool database reconstruction and testing. The methods disclosed herein include data-driven realization for both forward and inverse modeling to evaluate the simulation results in fluid composition and optical characterization and mutual-complementarily validate various multivariate calibrations and data mapping. The methods presented in this disclosure can be applied in real-time formation sampling and testing, such as prediction modification, uncertainty estimation, and unknown fluid identification. The combination of improved measurement systems and signal processing can enable a movement toward autonomous data generation for machine learning applied to downhole optical fluid analysis with minimized cost.

Some important results of database reconstruction as disclosed herein include an ensemble of added simulated spectra of 1,000 fluids from an external fluid compositional database to an internal database. Additional results include filling the missing or incomplete fluid composition and property data by using simulated spectra data and other available compositional data; refining fluid answer product calibration with reconstructed database, which exhibits better fluid diversity, and improving formation fluid sampling and testing through quality control (QC) enhancement with use of expanded database.

The fundamentals of optical spectrum reconstruction from fluid compositional databases are supported by the principles of the Beer-Lambert law, by which the optical spectrum of a particular substance, which is related to the absorption as a function of wavelength, can be defined as the sum of the linear responses of entire compositional concentrations of the substance. However, this correlation has been widely applied inversely in the practice of using surface and downhole optical measurements to estimate fluid compositions and properties. The advancement of machine learning combined with current domain knowledge makes data-driven analytics a reliable solution for many problems that are questionable and controversial, including the uncertainty of data consistency between internal and external databases, the replacement of missing data with simulation data, and the validation methods applied at the different levels of data mining and integration.

Several groups of forward, inverse, and spectrum reconstruction models are built in an existing internal database using complete information of fluid spectroscopies, compositions, and properties with neural network ensembles (NNEs). A typical existing internal database may have Optical-PVT full-range fluid spectral data; PSC data that are score values processed with standard PCA routines; and fluid compositional and property data. A database from an external oil and gas information source, however, may only have fluid composition and property data.

As used herein, a "sensor" refers to an optical sensor or any other sensor as disclosed herein may include at least one or more sensing elements. In some implementations, at least one of the sensing elements is an ICE designed to measure a fluid characteristic or property. According to some implementations, an ICE is essentially an optical interference-based device that can be designed to operate over a continuum of wavelengths in the electromagnetic spectrum from the visual (VIS) to mid-infrared (MIR) ranges, or any sub-set of that region.

As used herein, the term "optically interact" or variations thereof refers to the reflection, transmission, scattering, diffraction, or absorption of electromagnetic radiation either on, through or from one or more processing elements (i.e., ICE components) or a substance being analyzed by the processing elements.

The terms "tool" and "optical sensor" may be used herein interchangeably and refer generally to a sensor configured to receive an input of electromagnetic radiation that has interacted with a substance and produced an output of electromagnetic radiation from a sensing element arranged within or otherwise forming part of the optical computing device. The sensing element may be, for example, an ICE as described above. Prior to field use, the optical computing device, with each sensing element employed therein, is calibrated such that each output response can be used in conjunction with others to calculate fluid composition and properties through various signal transformation and characterization models upon being exposed to downhole conditions. Once calibrated, the optical computing device can be used in a wellbore operation, e.g., a drilling operation, a logging operation, a logging while drilling (LWD) operation, a wireline logging operation, another conveyance operation, or any other type of activity, such as a measuring while drilling (MWD) operation.

FIG. 1A depicts a schematic view of a logging operation deployed in and around a well system 1100a downhole in accordance with one or more implementations. The well system 1100a includes a logging system 1108 and a subterranean region 1120 beneath ground surface 1106. The well system 1100a can also include additional or different features that are not shown in FIG. 1A. For example, the well system 1100a can include additional drilling system components, wireline logging system components, or other components.

The subterranean region 1120 shown in FIG. 1A, for example, includes multiple subsurface layers 1122. The subsurface layers 1122 can include sedimentary layers, rock layers, sand layers, or any combination thereof and other types of subsurface layers. One or more of the subsurface layers can contain fluids, such as brine, oil, gas, or combinations thereof. A wellbore 1104 penetrates through the subsurface layers 1122. Although the wellbore 1104 shown in FIG. 1A is a vertical wellbore, the logging system 1108 can also be implemented in other wellbore orientations, such as horizontal wellbores, slant wellbores, curved wellbores, vertical wellbores, or any combination thereof.

The logging system 1108 also includes a logging tool 1102, a conveyance 1103, surface equipment 1112, and a computer system, also referred to herein as "computing subsystem 1110". As shown in FIG. 1A, the logging tool 1102 is a downhole logging tool that operates while disposed in the wellbore 1104. In some embodiments, the logging tool 1102 is suspended in the wellbore 1104 by the conveyance 1103. The conveyance 1103 can be wireline, slickline, coiled tubing, pipe, a downhole tractor, or a combination thereof that connects the logging tool 1102 to a surface control unit or other components of the surface equipment 1112. The surface equipment 1112 shown in FIG. 1A operates at or above the surface 1106, for example, near the well head 1105, to control the logging tool 1102 and possibly other downhole equipment or other components of the well system 1100a. All or part of the computing subsystem 1110 can be integrated with one or more components of, the surface equipment 1112, the logging tool 1102, or both.

The computing subsystem 1110 can be embedded in the logging tool 1102 (not shown), and the computing subsystem 1110 and the logging tool 1102 operate concurrently while disposed in the wellbore 1104. All or part of the computing subsystem 1110 may reside below the surface 1106, for example, at or near the location of the logging tool 1102.

The well system 1100a includes communication or telemetry equipment that allows communication among the computing subsystem 1110, the logging tool 1102, and other components of the logging system 1108. The logging system 1108 can include, but is not limited to, one or more systems and/or apparatus for wireline telemetry, wired pipe telemetry, mud pulse telemetry, acoustic telemetry, electromagnetic telemetry, or any combination of these and other types of telemetry.

Logging operations are performed in connection with various types of downhole operations at various stages in the lifetime of a well system and therefore structural attributes and components of the surface equipment 1112 and logging tool 1102 are adapted for various types of logging operations.

Figure 1B:
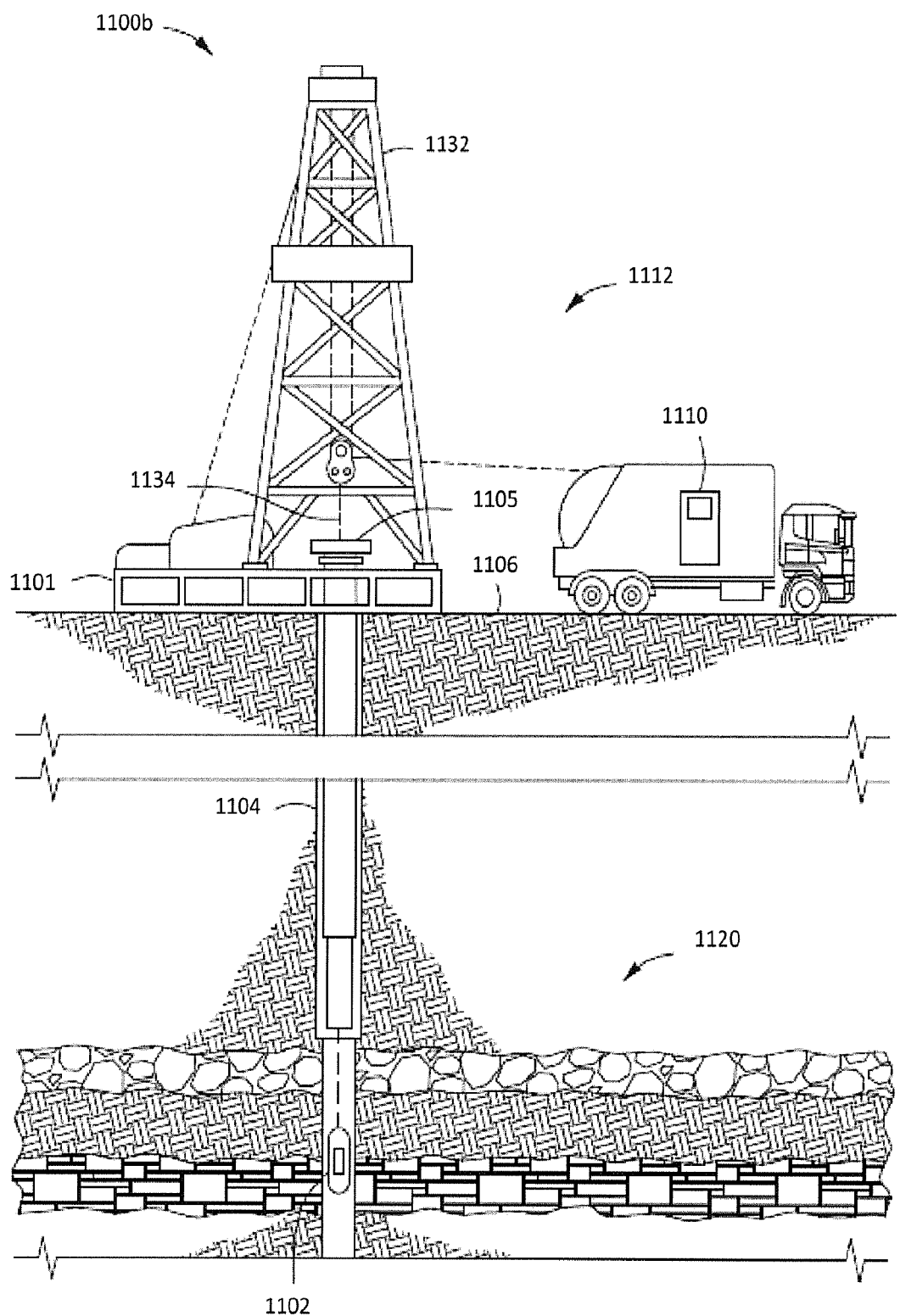

FIG. 1B depicts a schematic view of a wireline logging operation deployed in and around a well system 1100b in accordance with one or more implementations. The well system 1100b includes the logging tool 1102 in a wireline logging environment. The surface equipment 1112 includes, but is not limited to, a platform 1101 disposed above the surface 1106 equipped with a derrick 1132 that supports a wireline cable 1134 extending into the wellbore 1104. Wireline logging operations are performed, for example, after a drill string is removed from the wellbore 1104, to allow the wireline logging tool 1102 to be lowered by wireline or logging cable into the wellbore 1104.

In some embodiments, a well system 1100b can include the logging tool 1102 in a LWD environment in accordance with one or more implementations. Logging operation can be performed during drilling operations. Drilling is performed using a string of drill pipes connected together to form a drill string (not shown) that is lowered through a rotary table into the wellbore 1104. A drilling rig (not shown) at the surface 1106 supports the drill string, as the drill string is operated to drill a wellbore penetrating the subterranean region 1120. The drill string can include, for example, but is not limited to, a kelly, a drill pipe, a bottom hole assembly, and other components. The bottom hole assembly on the drill string can include drill collars, drill bits, the logging tool 1102, and other components. Exemplary logging tools can be or include, but are not limited to, MWD tools and LWD tools.

Figure 2:
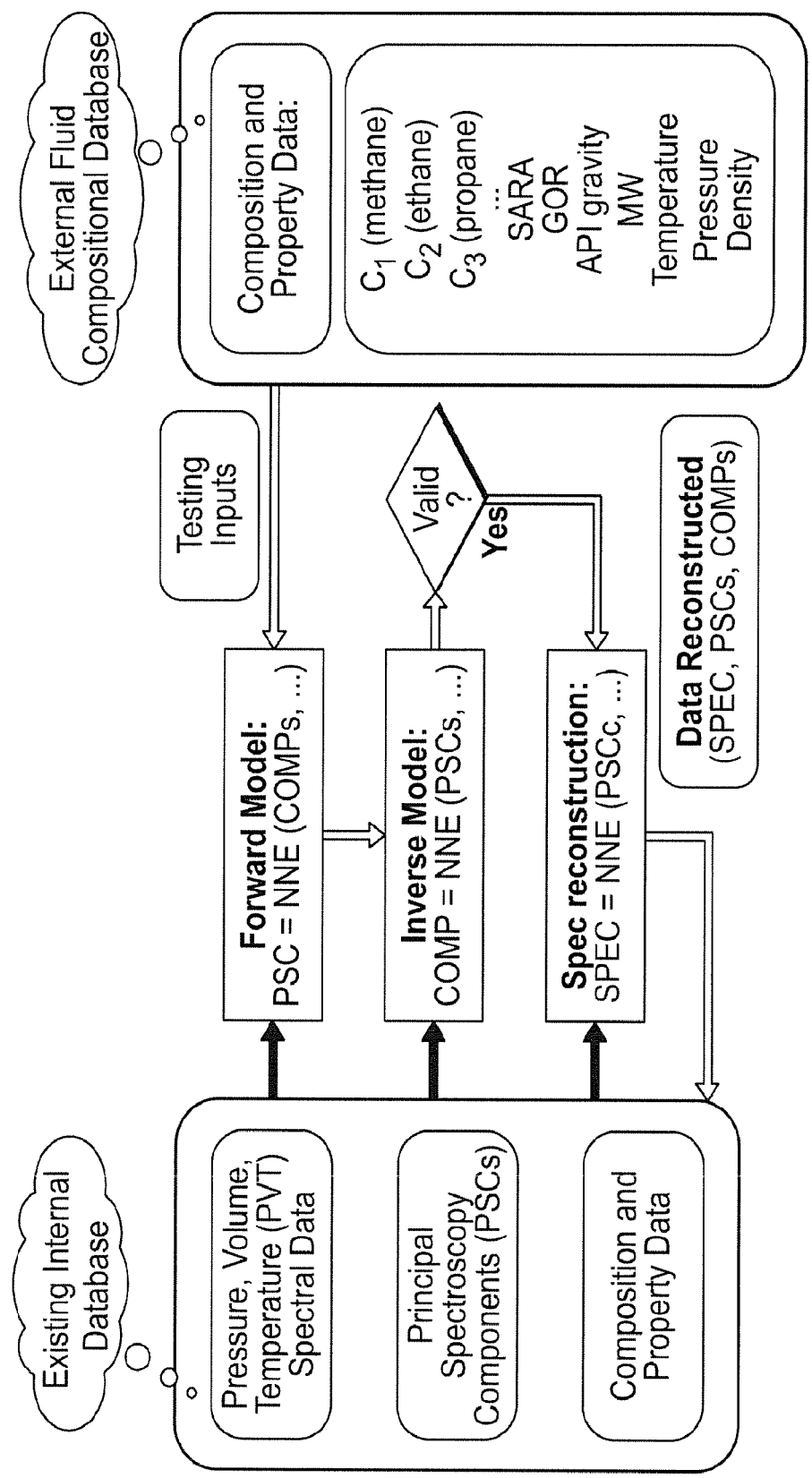
FIG. 2 shows a schematic overview of an example workflow for reconstructing optical principal spectroscopy component (PSC) and spectral data from an external source (e.g., publically available database) using available fluid compositional inputs.

FIG. 2 shows a schematic overview of a workflow diagram for spectra reconstruction method. As shown in FIG. 2, the method can include an existing internal database and an external source, such as an external fluid compositional database. The existing internal database can further include, but not limited to, pressure, volume, temperature spectral data, PSCs and compositional and property data. Similarly, the external fluid compositional database can include fluid compositional data, which can include carbon dioxide ($CO_2$), methane ($C_1$), ethane ($C_2$), propane ($C_3$), iso-butane ($iC_4$), n-butane ($nC_4$), iso-pentane n-pentane ($nC_5$), hexane plus ($C_{6+}$) where $C_{6+}$ is an approximation of a sum of chemical concentration of saturates, aromatics, resins, and asphaltenes (SARA), or hexanes ($C_6$), and heptane plus ($C_{7+}$). In some embodiments, fluid property and environmental parameters include molecular weight (MW), gas-oil ratio (GOR), API gravity, temperature, pressure, and density.

In some embodiments, the fluid compositional inputs can be from one of more external sources or databases. In other embodiments, the fluid compositional inputs can be from the existing internal database. In some embodiments, the spectra reconstruction can begin from external sources to recover missing PSC and spectral information using simulation results produced from one or more validated model predictions. In other embodiments, the forward models are used first to produce estimated PSC data with compositional inputs, such as fluid composition and property data as primary inputs from an external source. The inverse models then apply PSC estimates to generate predictions on fluid compositions and properties and compare the outputs to the measurement results on the fluid samples obtained from different field origins. The degree of matching between predicted fluid compositions and the target data in the external source suggests a level of consistency between the internal and external databases. It also indicates the direction to update the internal database and model base, including integrated data selection and additional effort of refining the current calibration on various inverse answer product predictive models to improve real-time downhole fluid analysis during formation and testing. In other embodiments, spectral reconstruction models take validated PSC and additional inputs from forward and inverse models and calculate VIS, NIR, and MIR fluid transmittance simulated outputs.

The simulation models can be constructed in the internal database and then introduced as the mutual-complementary testing method that uses forward and inverse models to validate data selection from external sources for database reconstruction. For example, a fluid compositional database can be used to demonstrate the developed methods and procedures and reconstruct the fluid optical spectral data.

Figure 3:
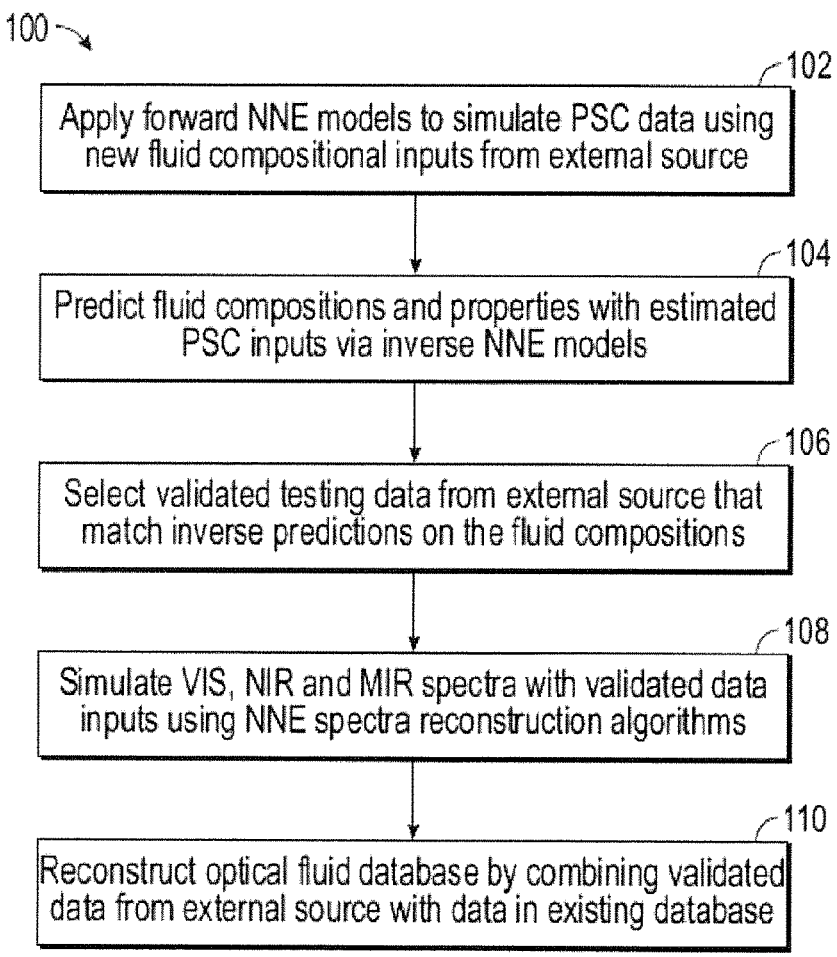
FIG. 3 is a flowchart for a fluid optical database reconstruction method in determining validated testing data from an external source for optical data reconstruction.

FIG. 3 presents a flowchart 100 showing a method for determining validated testing data from external source for optical data reconstruction. The method illustrated in FIG. 3 begins with step 102 for applying forward NNE models to simulate PSC data using new fluid compositional inputs from an external source. In this embodiment, fluid compositional inputs, such as those described above from an external source, are used in conjunction with NNE models. Applying appropriate NNE models with fluid compositional inputs can generate simulated PSC data.

Once simulated PSC data are obtained, the method further includes step 104 for predicting fluid compositions and properties with estimated PSC data via inverse NNE models. In this step, the PSC data are used as inputs via appropriate inverse NNE models to predict possible fluid compositions and their related properties.

When the possible fluid compositions and their related properties are obtained, step 106 selects validated testing data from the external source that match inverse predictions on the fluid compositions. In this step, the predicted possible fluid compositions and their related properties are compared with fluid compositions and/or their properties of the testing data that were used as forward model inputs in step 102. When one or more of the fluid compositions and their properties are matched with one or more of the fluid compositions from the external data base, the matched fluid compositions and their properties are considered validated testing data.

Based on the validated testing data, the method continues with step 108 for simulating VIS, NIR and MIR spectra with validated data inputs using NNE spectra reconstruction algorithms. In step 108, validated PSC data are used as inputs in conjunction with one or more of NNE spectra reconstruction algorithms to simulate the optical spectra ranging from VIS, NIR, and MIR spectra. Once simulated VIS, NIR, and MIR spectra are obtained, step 110 is configured for reconstructing optical fluid database by combining validated data from the external source with data in existing database. The reconstruction of the optical fluid database is considered achieved when the existing or internal database has added validated fluid compositional data and properties from the external source or database with simulated fluid spectra.

In one or more embodiments, a method includes providing fluid compositional data from a source; introducing the fluid compositional data into a computer system; applying at least one of a plurality of neural network ensemble (NNE) models to simulate principal spectroscopy component (PSC) data using the fluid compositional data; predicting fluid compositions and properties, wherein the predicting includes applying at least one of a plurality of inverse NNE models to the simulated PSC data; comparing the fluid compositional data with predicted fluid compositions and predicted properties; selecting a match between the fluid compositional data and the predicted fluid compositions and the predicted properties; validating matched fluid compositions and properties as validated testing data; applying at least one of a plurality of NNE spectra reconstruction algorithms to simulate visible (VIS), near infrared (NIR), and mid infrared (MIR) spectra using the validated testing data; and reconstructing an optical fluid database by combining the validated testing data into an existing database.

In some embodiments, the method further includes at least one of: designing of a multivariate optical element (MOE) or an integrated computation element (ICE) based on reconstructed optical fluid database; optimizing of an existing MOE or an existing ICE based on the reconstructed optical fluid database; or fabricating of a MOE or an ICE based on the reconstructed optical fluid database. In some embodiments, the method further includes updating calibration of a downhole optical sensor based on the reconstructed optical fluid database, and taking an optical measurement with the calibrated downhole optical sensor. In some embodiments, the method further reducing uncertainty in calibration or measurement data based on the reconstructed optical fluid database. In some embodiments, the method further includes facilitating sample contamination analysis based on the reconstructed optical fluid database. In some embodiments, the method further includes facilitating a wellbore operation based on the reconstructed optical fluid database.

In some embodiments, the source is at least one of: a database; laboratory results; or measurements from a tool or sensor. In some embodiments, the fluid compositional data includes at least one of: carbon dioxide ($CO_2$), methane ($C_1$), ethane ($C_2$), propane ($C_3$), iso-butane ($iC_4$), n-butane ($nC_4$), iso-pentane ($iC_5$), n-pentane ($nC_5$), and hexane plus ($C_{6+}$) where $C_{6+}$ is an approximation of a sum of chemical concentration of saturates, aromatics, resins, and asphaltenes (SARA), or hexanes ($C_6$), or heptane plus ($C_{7+}$). In some embodiments, the source is an external database, and the method further includes expanding the optical fluid database by merging data from a tool or sensor into the existing database. In some embodiments, the simulated visible (VIS), near infrared (NIR), and mid infrared (MIR) spectra includes a wavelength range from 450 nm to 3300 nm.

In embodiments utilizing the method as described above, forward and inverse models calibrated in the existing internal database for this application can form two groups of mutual complementing models that can validate each other. For example, each output parameter in one group can be estimated from the candidate inputs from the other group. Inverse (composition predictive) models can also be used to evaluate predictions of forward models for PSC data reconstruction. Forward (PSC predictive) models, on the other hand, can also be used to evaluate predictions of inverse models for fluid compositional data reconstruction if applied reversely.

In some embodiments, the forward modeling for optical data reconstruction might be limited by the availability of compositional data measurements in an external source. There might be variation in testing results among output variables in each group of models. Decision on validated sample selection for database reconstruction is based on the major components of the answer products. Remodeling with use of reconstructed data and other information is often required to refine calibrations, and the optical fluid database may grow through iterative development with inclusion of new measurement and simulation data each time. The autonomous data generation might eventually become possible when gaps in database are sufficiently filled with quality measurement and simulation entries.

Figure 4:
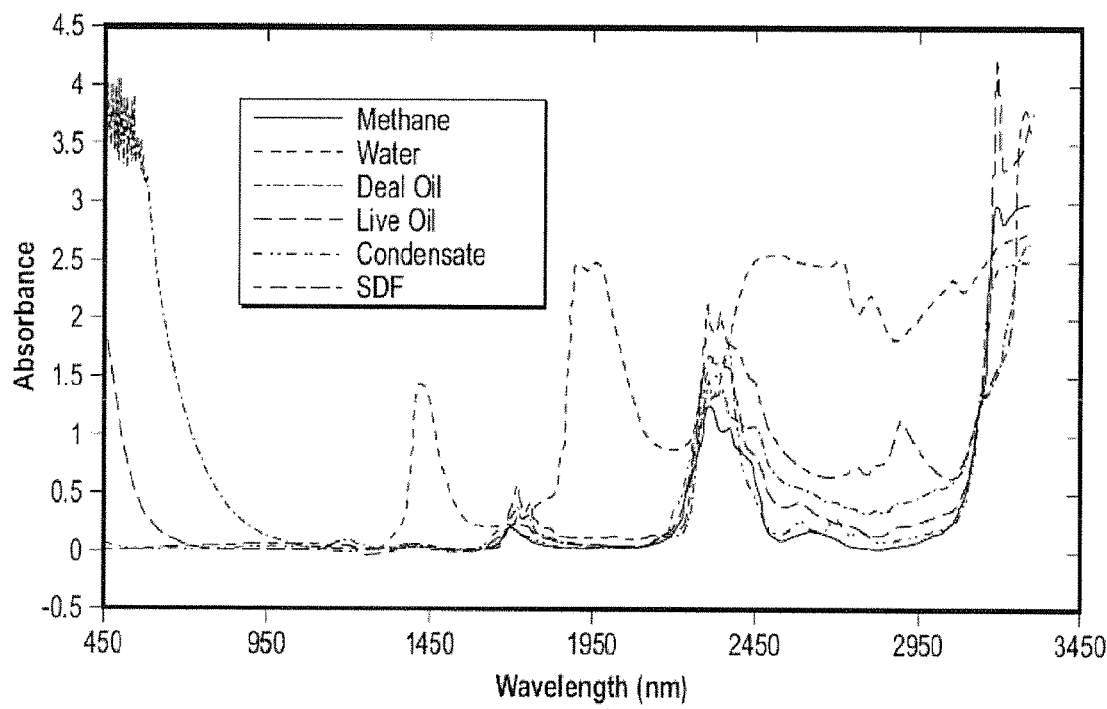
FIG. 4 shows optical absorbance spectra of typical fluid types covering the visible (VIS), near infrared (NIR) and mid infrared (MIR) wavelength range.
Figure 5:
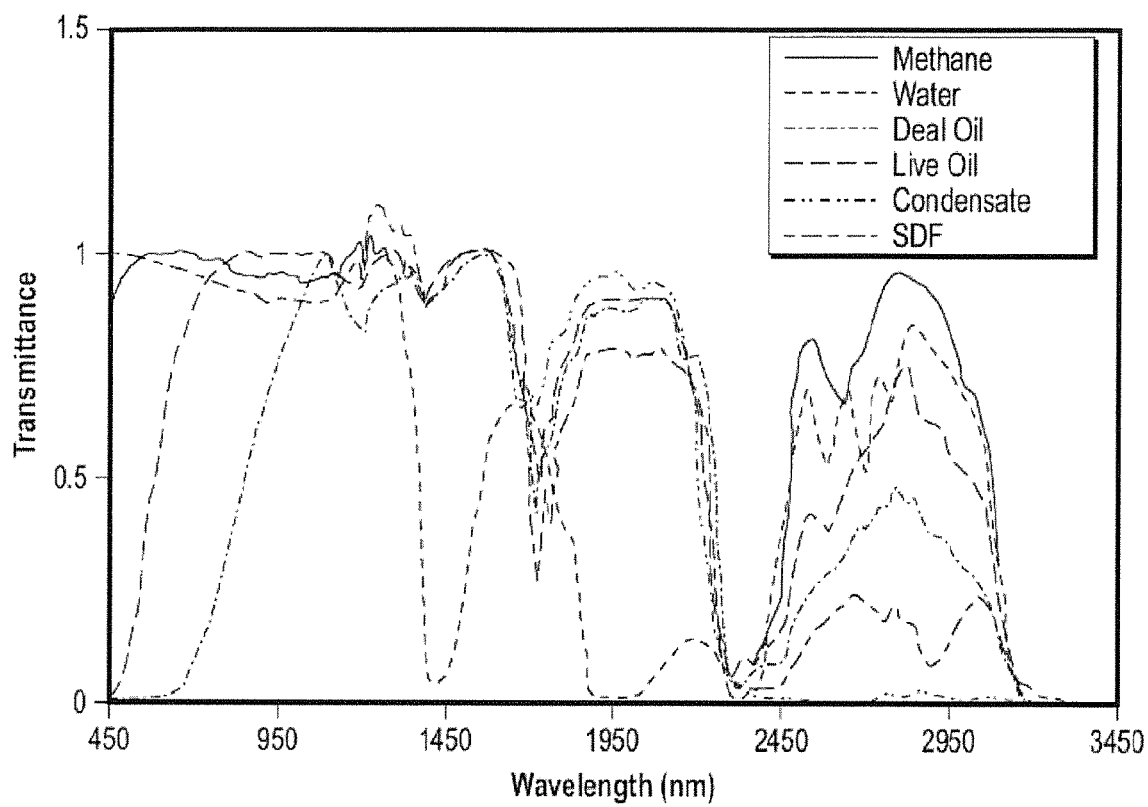
FIG. 5 shows optical transmittance spectra transformed from the absorbance data of the fluid types shown in FIG. 4.
Figure 6:
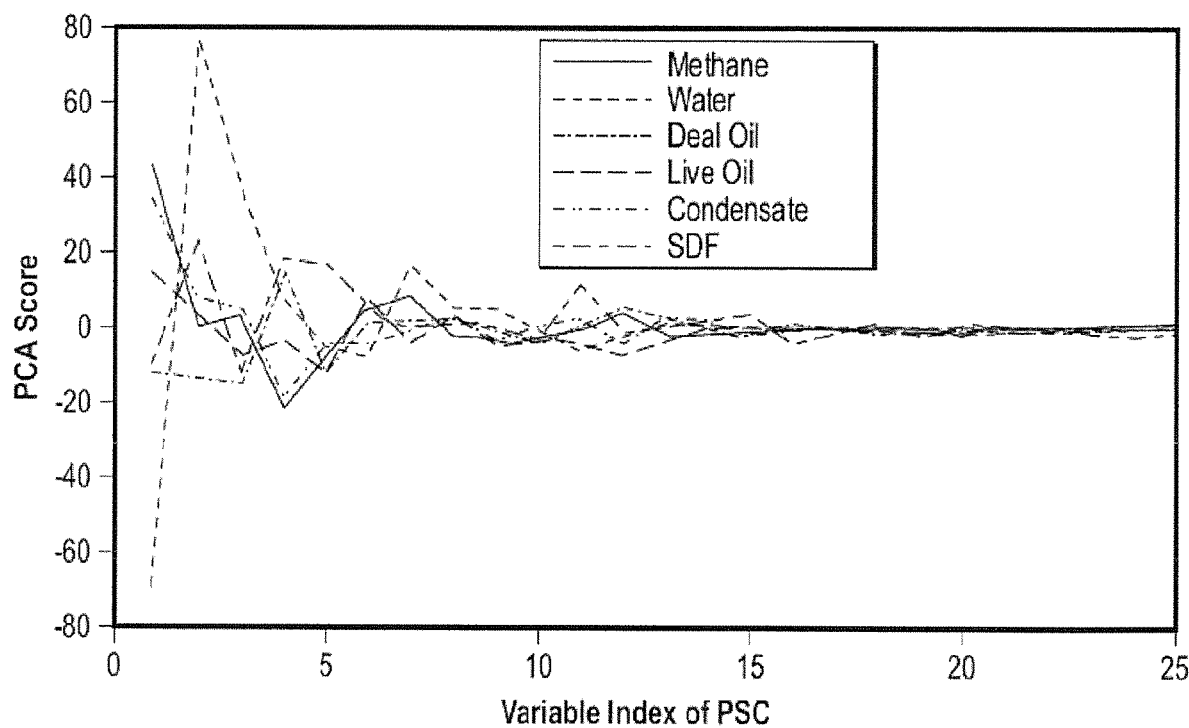
FIG. 6 shows principal component analysis (PCA) score values on the fluid types shown in FIG. 4 as a function of a variable index of PSC.

FIG. 4 shows the absorbance spectra of a few example fluid types, covering a wavelength range from 450 nm to 3300 nm. The fluid types shown in FIG. 4 include methane, water, dead oil (with only SARA compositions), live oil (natural oil under reservoir condition with dissolved hydrocarbon gas), condensate, and synthetic drilling fluid (SDF). The absorbance spectra are transformed to transmittance spectra first, which are more consistent with the optical sensor detector responses and processed with a PCA routine to obtain dimension-reduced PSC data. FIG. 5 shows optical transmittance transformed from the absorbance data of the fluid types shown in FIG. 4 covering the VIS, NIR, and MIR wavelength range. FIG. 6 displays the PCA score values of PSC parameters on the same selected samples shown in FIG. 4. The dimension-reduced PSC data are used as calibration outputs for forward modeling and calibration inputs for inverse modeling. Specifically, the dimension change from 2850 (assuming one nanometer resolution from 450 nm to 3300 nm) to 25 (the number of principal components selected) captures more than 99.5% variation of transmittance spectra. As for generic optical characteristics, PSC data can be used as calibration outputs for forward modeling and as calibration inputs for inverse modeling and spectrum reconstruction modeling.

Figure 7:
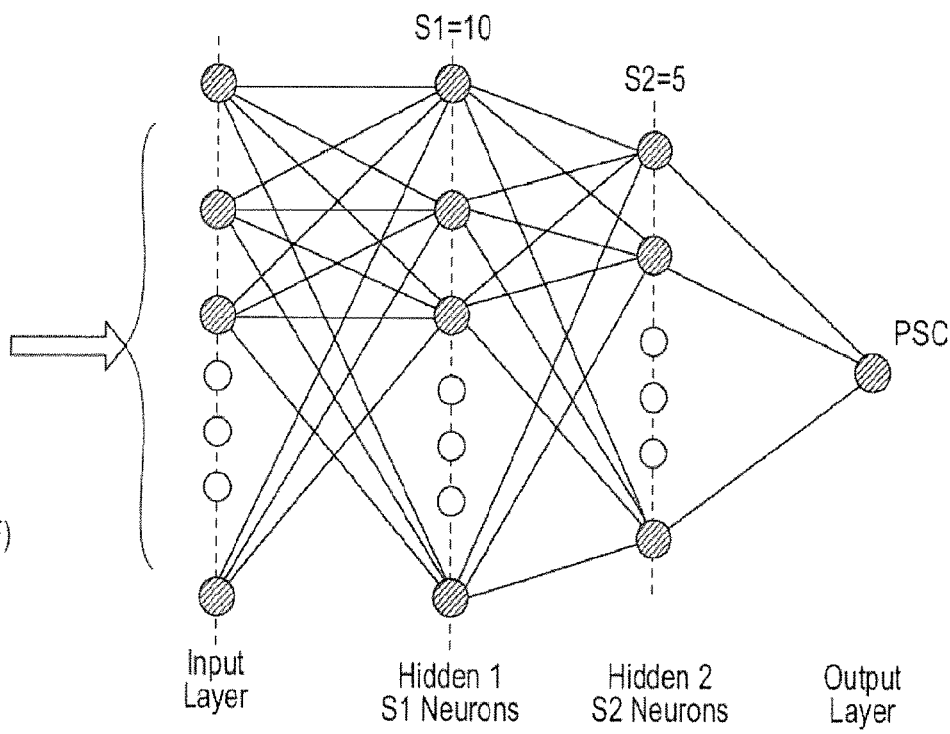
FIG. 7 illustrates empirical multi-input/single-output feedforward neural network structure applied to simulate each PSC parameter using fluid compositions and properties as candidate inputs. These candidates are processed for training variable-input neural networks.

FIG. 7 illustrates a typical forward model representation for this application using fluid primary compositions and properties as candidate inputs to simulate each PSC output with a standard multilayer feedforward neural network. The implementation is data-driven and nonlinear in general to ruggedize the mapping between the input and output variables that might be noise corrupted and imposed with complicated interfering factors. Some of the basic fluid compositional inputs, for example, for forward modeling, include carbon dioxide ($CO_2$), methane ($C_1$), ethane ($C_2$), propane ($C_3$), iso-butane ($iC_4$), n-butane ($nC_4$), iso-pentane ($iC_5$), n-pentane ($nC_5$), hexanes ($C_6$), and heptane plus ($C_{7+}$). The fluid property and environmental parameter include molecular weight (MW), gas-oil ratio (GOR), API gravity, temperature, pressure, and density are also used as candidate inputs, depending on the data availability and quality in the internal and external database.

The candidate inputs listed previously might not be completely used as the actual inputs in predicting every PSC parameter. Additionally, each PSC may not be estimated with single neural network realization with fixed inputs. The simulation algorithm is implemented to create a model base for estimating each PSC and to construct an NNE for reducing the risk of inadvertently applying a single neural network that is rendered statistically inferior as a result of local minimum from initialization, lack of generalization, and other uncertainties associated with network configuration and data partitioning.

Figure 8:
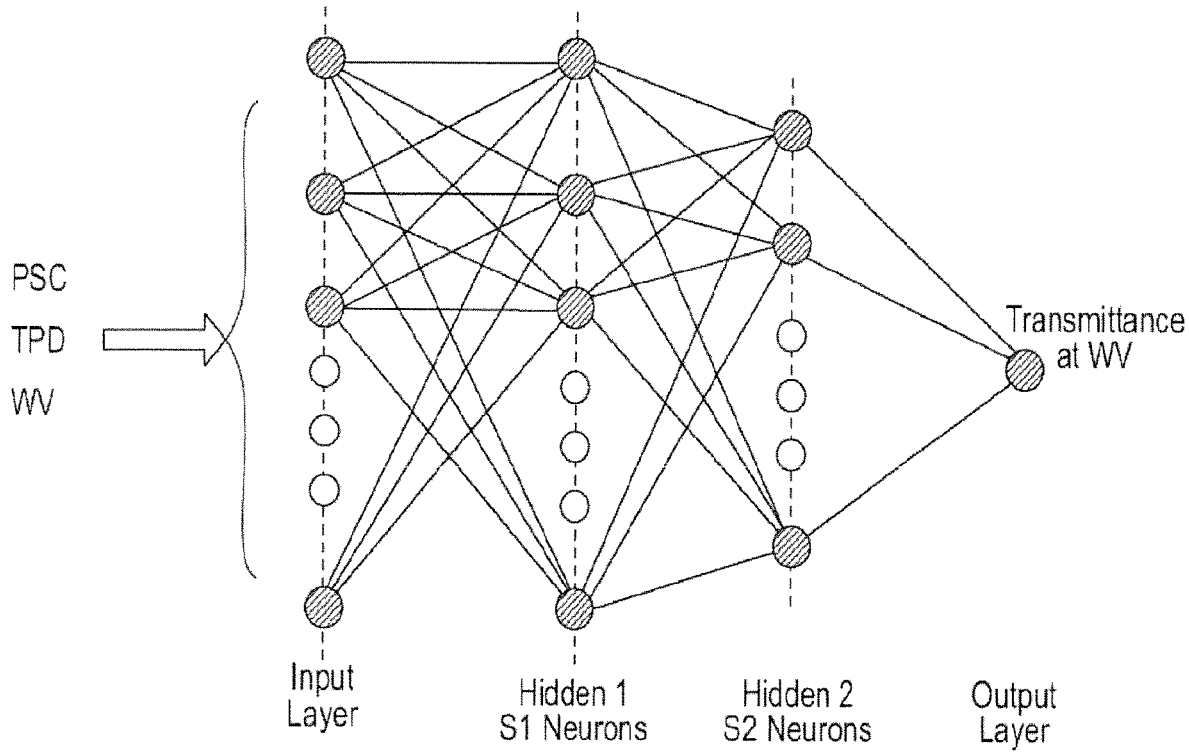
FIG. 8 illustrates a neural network structure for spectrum reconstruction.

FIG. 8 illustrates a neural network structure for spectrum reconstruction. The neural network simulator produces the estimated value of transmittance with desirable resolution for any given wavelength input specified by the application range. The candidate inputs of the model include PSC parameters and environmental parameters (fluid temperature, pressure, and density). In this example implementation, wavelength (WV) in nanometer scale is used as an additional variable with other candidate inputs, including PSC parameters and temperature, pressure, and density, to simulate the transmittance value corresponding to each specific wavelength. Although PSC data set is proceed with full-range spectra in modeling, it can be used as cross-band inputs to construct VIS, NIR, and MIR spectra reconstruction models with different NNEs separately, with each NNE algorithm performing data reconstruction on the focused range. Depending on the features and reconstruction complexity in each spectral range, the basic neural network structure parameter S1 (the number of neurons on the first hidden layer) and S2 (the number of neurons on the second hidden layer) is set to 10 and 5 for VIS spectra reconstruction and 20 and 10 for NIR and MIR spectra reconstruction, respectively. In some implementation, the process retains calibration effort again with a backward stepwise input selection routine applied to all candidate variables except the WV input, which has to be used for each member network to calculate transmittance. For downhole fluid analysis using optical sensor measurements, NNE is only built with a smaller number of member networks to reduce the computational cost in real-time data processing. For offline database reconstruction, NNE performance can be optimized by adjusting member network selection, as necessary. It has been demonstrated that once the validated PSC data estimation is justified, the quality spectrum construction can be achieved with NNE consisting of only three member networks.

In some implementations, the forward and inverse models developed in the internal database are applied as candidate member networks to optimize NNE construction to simulate the missing optical data of an external database and reconstruct an expanded database with validated mapping from the external source. This approach is different from real-time downhole fluid analysis. While real-time downhole fluid analysis requires pre-job decisions on model selection and applies predetermined models to estimate unknown reservoir fluid properties, database reconstruction allows delving into the entire model base to determine the validated mapping and maximize the compatibility of measurement and simulation data.

In other implementations, testing data used are obtained from a publically available database, which includes both global geo-PVT and geochemical fluid information. In such database, the actual C1 and $C_{6+}$ data range over approximately 1,000 testing samples from different reservoirs. Following the workflow illustrated in FIG. 2, the degree of fluid composition consistency in two databases is evaluated first. It is assumed that the validated PSC data estimation from the forward model calculation will reproduce matched primary fluid compositions and properties on the testing data through inverse model simulation, if measurements in both databases are compatible and the simulation models are selected properly. To reduce the uncertainty of PSC data estimation, the mutual-complementing model simulation is applied iteratively using a genetic algorithm, which evolutionarily optimizes NNE member network selection for each predictive model by minimizing the error in final inverse model predictions on major fluid compositions and properties $C_1$, $C_2$, $CO_2$, $C_{6+}$, density, and API. This can be performed by evolving member network selection from a candidate pool for each NNE in forward PSC computation (given the inverse NNEs are unchanged), evolving NNE construction for major fluid answer products (given the estimated PSC data is constant), or evolving member network selection for both forward and inverse models in a batch optimization mode.

In one or more embodiments, evolutionary optimization with a genetic algorithm uses binary string code to represent each five-member NNE, and the optimization is population based to minimize the ranked overall prediction error on a large number of testing data of reproduced major fluid answer products using genetic operators, such as selection, mutation, and crossover. During evolutionary computation, the update of PSC ensemble output in each generation is performed by recalculating the arithmetic average based on the member network selection in each chromosome update, and the forward model computation is not included in the loop of evolutionary optimization because PSC outputs of testing data for each candidate member network are already available through preprocessing. The ensemble output update for each answer product, however, has to undergo population-based inverse model data processing, which is a function of NNE outputs of forward modeling and a function of NNE member network selection of inverse modeling.

Figure 9A:
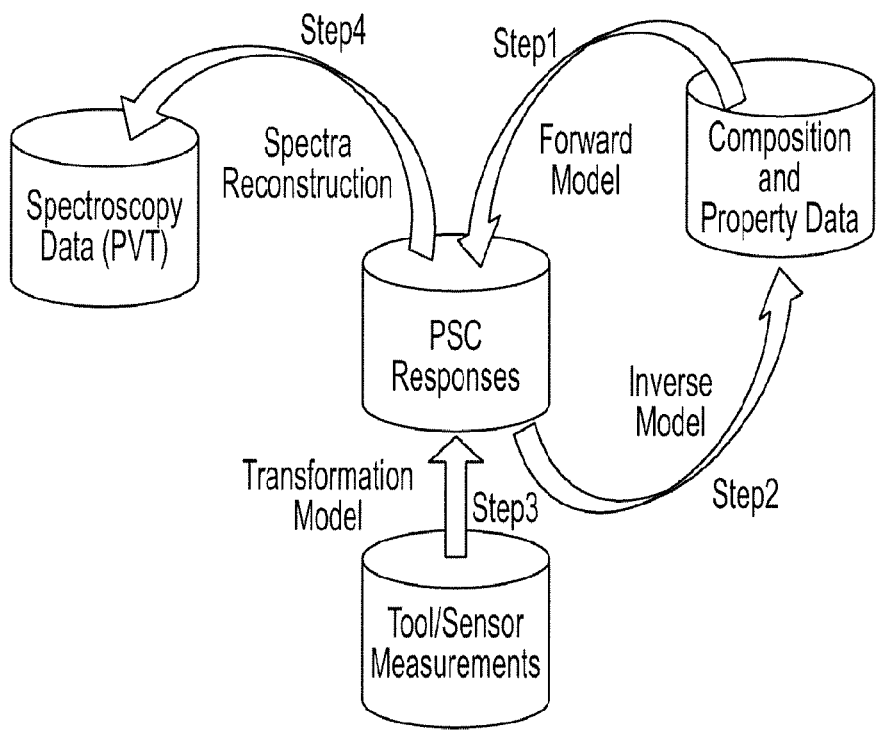
FIG. 9A illustrates an embodiment of a fluid optical database reconstruction method with use of available field optical sensor measurement data and known fluid sample compositions.

FIG. 9A illustrates an embodiment of a fluid optical database reconstruction method. The embodiment shown in FIG. 9A is a variation of the embodiment shown in FIG. 3. The embodiment illustrated in FIGS. 9A and 9B utilize available lab results similarly to using compositional data from an external source; the mutual complementary model validation method discussed in previous embodiment from FIG. 3, therefore, still applies. A novel aspect in the embodiment of FIG. 9A is taking estimated PSC data, if validated, as new reference fluid responses which can be used in conjunction with field sensor data to improve the diversity of existing reference fluids, enabling more robust calibration for optical sensor data transformation.

Figure 9B:
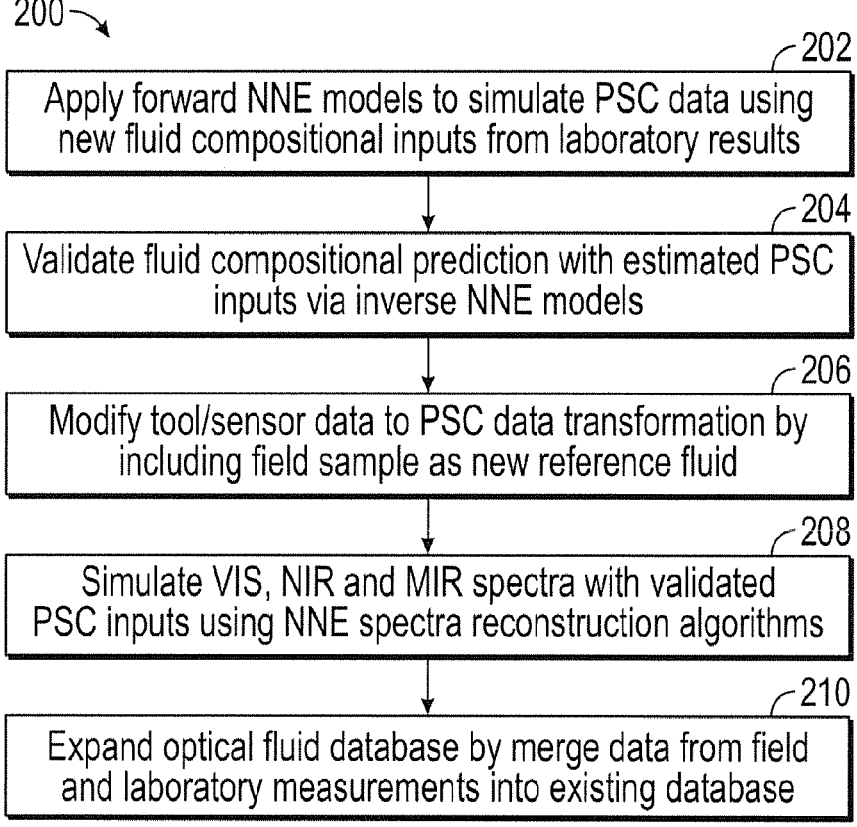
FIG. 9B is a flowchart showing the steps of the embodiment shown in FIG. 9A.

FIG. 9B presents a flowchart 200 showing the steps of the embodiment shown in FIG. 9A of the fluid optical database reconstruction method. The method illustrated in FIG. 9B begins with step 202 for applying forward NNE models to simulate PSC data using new fluid composition inputs from laboratory results (i.e., experimental results). In this embodiment, fluid compositional inputs, such as those described above from laboratory results, are used in conjunction with NNE models. Applying appropriate NNE models with fluid compositional inputs can generate simulated PSC data. The step 202 is different from step 102 in that step 202 utilizes fluid compositional inputs from laboratory results whereas step 102 utilizes fluid compositional inputs from an external source.

Once simulated PSC data are obtained, the method further includes step 204 for validating fluid compositional prediction with estimated PSC inputs via inverse NNE models. In this step, the PSC data are used as inputs via appropriate inverse NNE models to validate fluid compositional predictions.

When fluid compositional predictions and their related properties are validated, step 206 is directed to modify tool and/or sensor data to PSC data transformation by including field sample as a new reference fluid. In other words, the fluid compositional data from laboratory results are used for introducing a new reference fluid in the transformation of PSC data. Based on the transformed PSC data, the method continues with step 208 for simulating VIS, NIR, and MIR spectra with validated PSC inputs using NNE spectra reconstruction algorithms. In step 208, validated PSC inputs are used in conjunction with one or more of NNE spectra reconstruction algorithms to simulate the optical spectra ranging from VIS, NIR, and MIR spectra. Once simulated VIS, NIR, and MIR spectra are obtained, step 210 is configured for expanding optical fluid databases by merging data from the field and/or laboratory results with data in an existing database. The reconstruction and/or expansion of the optical fluid database is achieved when the existing or internal database has expanded to include additional fluid compositional data and properties with simulated spectra from the field and/or laboratory results into one or more existing databases.

Figure 10A:
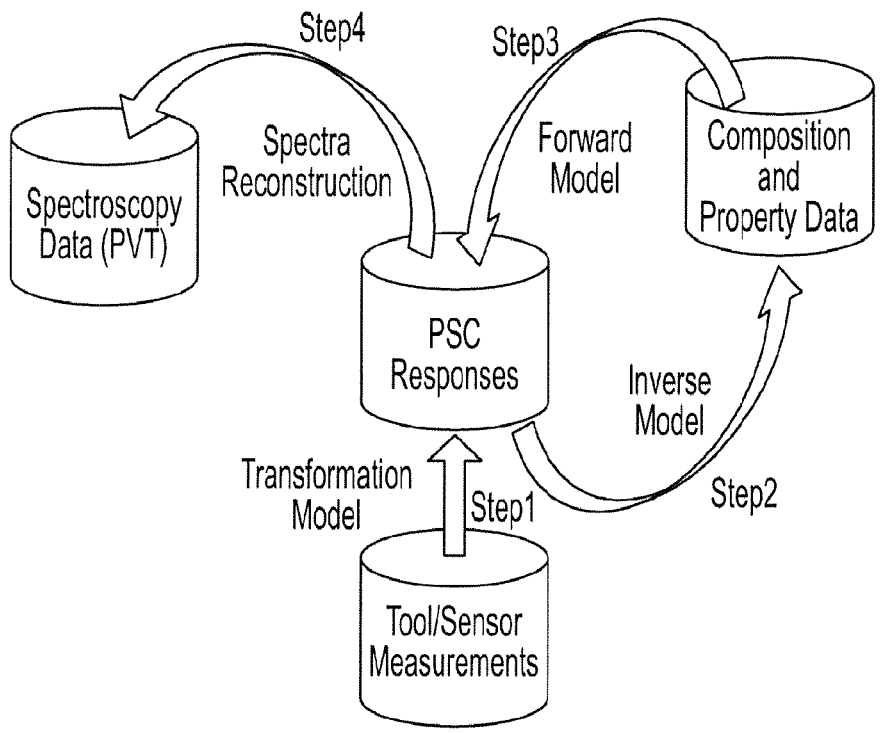
FIG. 10A illustrates another embodiment of a fluid optical database reconstruction method using available field optical sensor measurement data and unknown fluid sample compositions.

FIG. 10A illustrates another embodiment of a fluid optical database reconstruction method that includes optical tool measurement data and post-processed model prediction data on field samples into an empirical database. The focus of this embodiment is to ruggedize PSC estimation by iteratively improving prediction agreement of forward models and optical sensor data transformation models with unknown fluid composition and property data. For instance, the forward NNE models may use modified predictions from initial inverse model outputs in Step 2 to make data entries self-consistent in Step 3, and transformation model may need to re-calibrate if PSC parameter estimation is updated after Step 3 and validated with use of inverse models in Step 2 again.

Figure 10B:
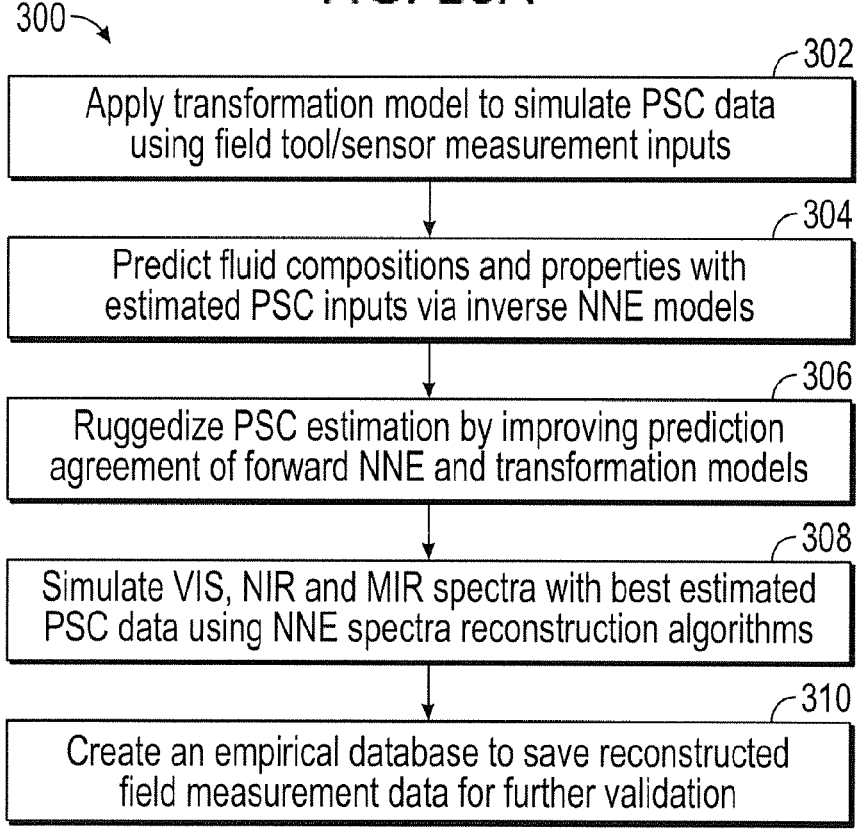
FIG. 10B is a flowchart showing the steps of the embodiment shown in FIG. 10A.

FIG. 10B presents a flowchart 300 showing the steps of the embodiment shown in FIG. 10A of the fluid optical database reconstruction method. The method illustrated in FIG. 10B includes step 302 for applying transformation model to simulate PSC data using field tool and/or sensor measurement inputs. In this embodiment, field tool and/or sensor measurement inputs, such as those described above, are used in conjunction with one or more transformation models. Applying one or more appropriate transformation models with measurement inputs can generate simulated PSC data. The step 302 is different from step 202 or step 102 in that step 302 utilizes field tool and/or sensor measurement inputs, whereas step 202 utilizes fluid compositional inputs from laboratory results and step 102 utilizes fluid compositional inputs from an external source.

Once simulated PSC data are obtained, the method further includes step 304 for predicting fluid compositions and properties with estimated PSC data via inverse NNE models. In this step, the PSC data are used as inputs via appropriate inverse NNE models to predict possible fluid compositions and their related properties. At step 306, the method includes ruggedizing PSC estimation by improving prediction agreement of forward NNE and transformation models. In this step, improving the prediction agreement between forward NNE and transformation models can provide higher confidence in simulating PSC data so as to achieve the best estimated PSC data. Based on the data from step 306, the method continues with step 308 for simulating VIS, NIR and MIR spectra with best estimated PSC data using NNE spectra reconstruction algorithms. In step 308, best estimated PSC data are used as inputs in conjunction with one or more of NNE spectra reconstruction algorithms to simulate the optical spectra ranging from VIS, NIR, and MIR spectra. Once simulated VIS, NIR, and MIR spectra are obtained, step 310 is configured for creating an empirical database to save reconstructed field measurement data for further validation. In this embodiment, the reconstructed field measurement data can be added to existing databases and additional validation efforts can lead to more ruggedized databases.

In some embodiments, a method includes measuring a sample with an optical sensor to provide measurement data; introducing the measurement data into a computer system; applying at least one of a plurality of transformation models to simulate PSC data using the measurement data; ruggedizing the simulated PSC data by comparing at least one of a plurality of NNE models and the at least one of the plurality of transformation models to produce an agreement, thereby producing a best estimated PSC data; applying at least one of a plurality of NNE spectra reconstruction algorithms to simulate VIS, NIR, and MIR spectra using the best estimated PSC data; producing reconstructed field measurement data based on the application of the at least one of the plurality of NNE spectra reconstruction algorithms; and creating an empirical database to save the reconstructed field measurement data.

In some embodiments, the method further includes facilitating a wellbore operation based on the reconstructed field measurement data. In another embodiment, the measurement data includes at least one of: carbon dioxide ($CO_2$), methane ($C_1$), ethane ($C_2$), propane ($C_3$), iso-butane ($iC_4$), n-butane ($nC_4$), iso-pentane ($iC_5$), n-pentane ($nC_5$), and hexane plus ($C_{6+}$) where $C_{6+}$ is an approximation of a sum of chemical concentration of saturates, aromatics, resins, and asphaltenes (SARA), or hexanes ($C_6$), or heptane plus ($C_{7+}$). In some embodiments, the reconstructed field measurement data is added to an existing database. In some embodiments, the simulated visible (VIS), near infrared (NIR), and mid infrared (MIR) spectra includes a wavelength range from 450 nm to 3300 nm.

The general methods described herein can be applied to, for example, an implementation involving MIR spectra reconstruction and adaptive local regression model for accurately estimating oil-based mud (OBM) contamination and endmember spectral fingerprints. Contamination estimation of OBM drilling fluid filtrate contamination in petroleum is one of the challenges in obtaining laboratory quality open hole formation tester samples. OBM filtrate contamination includes either petroleum distillate base oil, or synthetic base oil. In some embodiments, the synthetic based oil includes olefins and/or esters which are MIR active. MIR optical region from 2450 nm to 3300 nm affords a high contrast between formation fluid and synthetic drilling fluid filtrate and petroleum, but that contrast is highly inconsistent dependent on either the synthetic drilling fluid base oil source, or the nature of the petroleum. A measurement accuracy of +/−4 wt % filtrate can be achieved for a generic regression designed to work for OBM/petroleum combinations, which can degrade to +/−6 wt % if the OBM filtrate is not included in the calibration set. When a calibration specifically designed with a near matching drilling fluid filtrate and a close formation fluid type are applied, the performance improves to 1.1 wt % accuracy.

In some embodiments, an adaptive local calibration method includes analysis of sufficiently similar filtrate and formation fluid pairs. The method includes the use of an adaptive neural network to fingerprint both formation fluids and a set of filtrates. The fingerprint is designed to operate simultaneously on the VIS, NIR, and MIR. In some embodiments, the adaptive local calibration method for synthetic drilling fluid filtrate can include reconstructing MIR spectra of evolving fluid mixtures during cleanup using real-time multiple sensor data. It also includes using simple linear function or nonlinear artificial neural networks (ANNs) to fingerprint the endmembers, for example, mud filtrates and clean formation fluids, and optimizing PSC inputs. In some embodiments, the method further includes iteratively refining nearest neighbor estimates in real-time synthetic mixing for calibration construction. This can provide residual estimates for confidence of calibration. Further, the method is far more efficient and accurate than a generic global calibration. Therefore, an accurate contamination estimation can facilitate improvement and improved estimation of clean formation fluid properties (either spectra fingerprints, geochemistry, or PVT properties) can help in gaining further understanding of reservoir architecture, for example, continuity, compartmentalization, fluid grading, etc., among many other technical information.

In some embodiments, the spectra reconstruction method is used to reconstruct the spectra (both MIR and VIS spectra) of contaminated fluids. Based on the evolution of the spectra patterns during the cleanup process, three closest nearest neighbor formation fluids and filtrates are identified and selected from an existing filtrate and formation fluid spectra library. In some embodiments, an ANN-PSC calibration can be developed with 9 formation fluid-filtrate sets of the 3×3 fluid sets, each from sufficiently high contamination, for example, ranging from 70% contamination to pure formation fluid, for example, 0% contamination. In another embodiment, the PSC level can be automatically adjusted to capture the greatest variation of the pumpout trend while minimizing the residual. A first contamination estimate and pure endmember (filtrate and formation fluid) estimate is then provided. In other embodiments, a next iteration of 3 closest filtrate and formation fluids are selected to proceed. A new set of three closest nearest neighbor formation fluids and filtrates are then selected and repeated until the contamination curve estimate is stable within a desired tolerance of about 2%.

In some embodiments, the fingerprinted proxy selection of filtrate and/or formation fluid can be accomplished with alternate means, such as but not limited to, a predetermined number of nearest neighbors. An objective of using at least 3 filtrates and 3 formation fluids is to allow simplification of the process of refining the proxy fluid selections and to allow effective interpellation of the calibration curve among the closest nearest neighbors. Use of many more fluids for calibration may decrease the accuracy of the analysis, where as too few may provide insufficient calibration.

Figure 11:
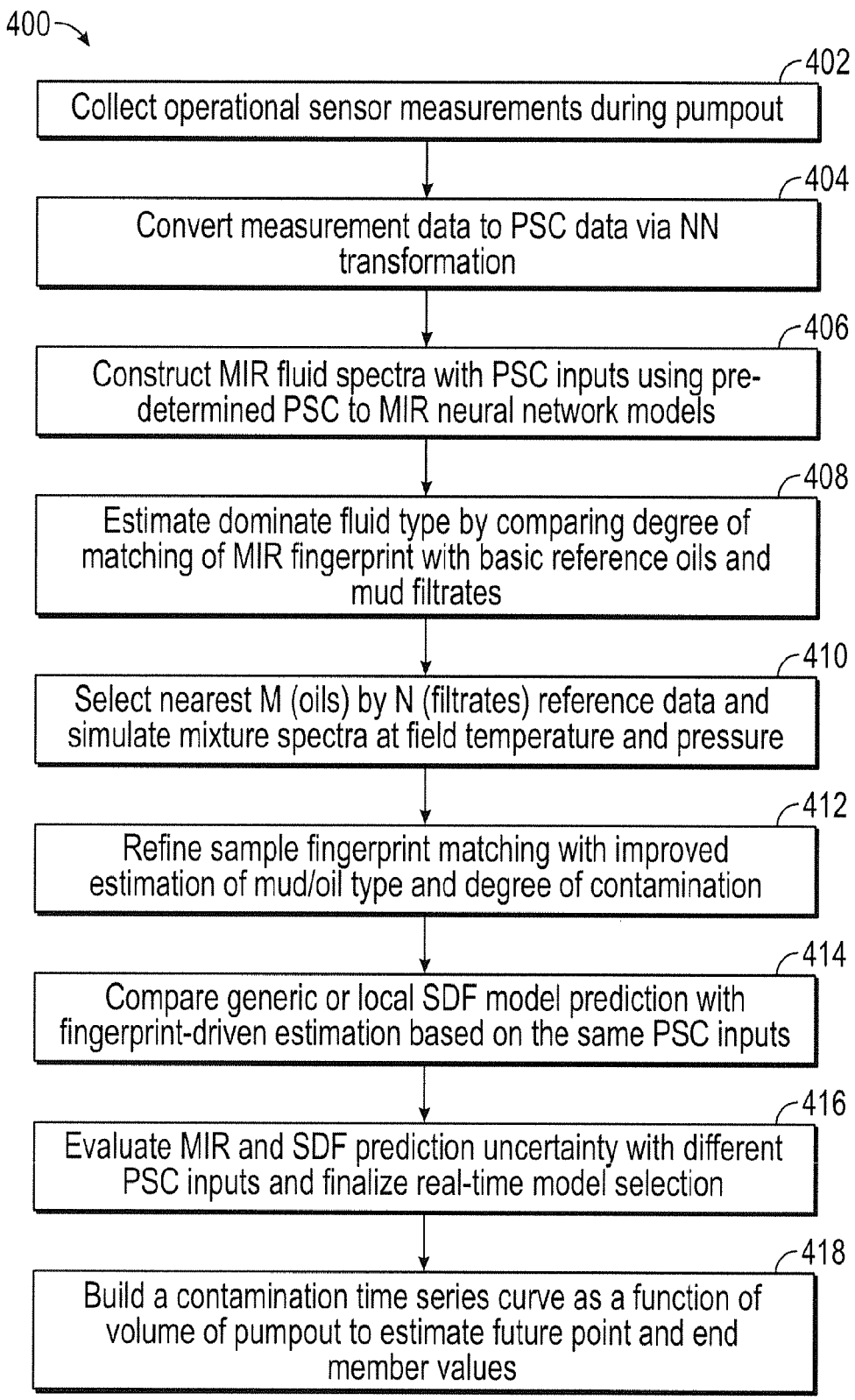
FIG. 11 is a flowchart of alternative fluid spectra feature extraction for estimating pumpout contamination.

FIG. 11 presents a flowchart 400 for an embodiment of alternative fluid spectra feature extraction for estimating pumpout contamination. The method illustrated in FIG. 11 includes step 402 for collecting operation sensor measurements (measurement data) during pumpout, followed by step 404 for converting measurement data to PSC data via neural network transmation, followed by step 406 for constructing MIR fluid spectra with PSC inputs using pre-determined PSC to MIR neural network models, followed by step 408 for estimating dominant fluid type by comparing degree of matching of model produced MIR fingerprint with profiles of basic reference oils and mud filtrates, followed by step 410 for selecting nearest M (oils) by N (filtrates) reference data and simulating mixture absorbance spectra through various linear combinations at field temperature and pressure, followed by step 412 for refining sample fingerprint matching with improved estimation of mud/oil type and degree of contamination, followed by step 414 for comparing generic or local synthetic drilling fluid (SDF) model prediction with spectral fingerprint-driven estimation based on the same PSC inputs, followed by step 416 for evaluating MIR and SDF model prediction uncertainty by different PSC inputs and finalizing real-time model selection, and finally followed by step 418 for building a contamination time series curve as a function of volume of pumpout to estimate future point and end member values.

In some embodiments, the method includes measuring a sample with an optical sensor to provide operational sensor measurement data; introducing the operational sensor measurement data into a computer system; converting, via the computer system, the operational sensor measurement data to PSC data via at least one of a plurality of neural network models; constructing MIR fluid spectra with the PSC data using at least one of pre-determined PSC to MIR neural network models, the constructed MIR fluid spectra resulting in a MIR fingerprint; estimating a dominant fluid type by comparing a degree of matching between the MIR fingerprint and spectra of reference oils and mud filtrates; selecting nearest M oils by N filtrates reference data and simulate a mixed spectra at field temperature and pressure; determining the degree of matching between the MIR fingerprint and the simulated mixed spectra of M oils and N filtrates; and formulating a degree of contamination based on the degree of matching between the MIR fingerprint and simulated mixed spectra of M oils and N filtrates.

In other embodiments, the method further includes comparing synthetic drilling fluid (SDF) model with the degree of contamination based on the MIR fingerprint, the simulated mixed spectra of M oils and N filtrates, and the PSC data. In other embodiments, the method includes evaluating MIR and SDF model prediction uncertainty by different PSC inputs and finalizing real-time model selection. In other embodiments, the method further includes building a contamination time series curve as a function of volume of pumpout to estimate future point and end member values.

In some embodiments, M and N can be any integer number between 1 to 30, any integer number between 1 to 30, and any integer number between 1 to 10. In some embodiments, M and N can be any integer number between 2 and 7, any integer number between 2 and 6, any integer number between 3 and 5. In some embodiments, M is 3 and N is 3.

In other embodiments, the determining the degree of matching between the MIR fingerprint and the simulated mixed spectra of M oils and N filtrates is repeated until the degree of contamination is stable within a desired tolerance of about 2%. In some embodiments, the method further includes facilitating a wellbore operation based on the degree of contamination. In some embodiments, the constructed MIR fluid spectra includes a wavelength range from 2450 nm to 3300 nm.

In other embodiments, the steps for calibration update on newly selected reference data each time in main embodiment is replaced by mixture spectra simulation at field temperature and pressure. This alternative approach further reduces the number of reference spectra with different mud/oil combinations, and would simplify the nearest neighbor based fingerprint matching. For PSC input optimization, the alternative approach may also use existing model base pre-determined with different PSC inputs to finalize real-time MIR and SDF model selection. To apply the method in the flowchart 400, all candidate MIR and SDF predictive models and reference fluid spectra of basic oils and mud filtrates are imported to a computer system (e.g., a processor or data processor) of downhole tool in a wellbore operation and available for model and spectra selection in real-time data processing.

Application of the models described above, such as NNE, forward and inverse neural networks, can be performed on a computer system. In certain aspects, the computer system may be implemented using one or more pieces of hardware or a combination of software and hardware, either in a dedicated server, integrated into another entity, or distributed across multiple entities.

What is claimed is:

1. A method, comprising:
providing fluid compositional data from a source;
introducing the fluid compositional data into a computer system;
applying at least one of a plurality of neural network ensemble (NNE) models to simulate principal spectroscopy component (PSC) data using the fluid compositional data;
predicting fluid compositions and properties, wherein the predicting includes applying at least one of a plurality of inverse NNE models to the simulated PSC data;
comparing the fluid compositional data with the predicted fluid compositions and predicted properties;
selecting a match between the fluid compositional data and the predicted fluid compositions and the predicted properties;
validating matched fluid compositions and properties as validated testing data;
applying at least one of a plurality of NNE spectra reconstruction algorithms to simulate visible (VIS), near infrared (NIR), and mid infrared (MIR) spectra using the validated testing data; and
reconstructing an optical fluid database by combining the validated testing data into an existing database.

2. The method of claim 1, further comprising at least one of:
designing of a multivariate optical element (MOE) or an integrated computation element (ICE) based on reconstructed optical fluid database;
optimizing of an existing MOE or an existing ICE based on the reconstructed optical fluid database; or fabricating of a MOE or an ICE based on the reconstructed optical fluid database.

3. The method of claim 1, further comprising:
updating calibration of a downhole optical sensor based on the reconstructed optical fluid database, and taking an optical measurement with the calibrated downhole optical sensor.

4. The method of claim 1, further comprising:
reducing uncertainty in calibration or measurement data based on the reconstructed optical fluid database.

5. The method of claim 1, further comprising:
facilitating sample contamination analysis based on the reconstructed optical fluid database.

6. The method of claim 1, wherein the source is at least one of: a database; laboratory results; or measurements from a tool or sensor.

7. The method of claim 1, wherein the fluid compositional data includes at least one of: carbon dioxide ($CO_2$), methane ($C_1$), ethane ($C_2$), propane ($C_3$), iso-butane ($iC_4$), n-butane ($nC_4$), iso-pentane ($iC_5$), n-pentane ($nC_5$), and hexane plus ($C_{6+}$) where $C_{6+}$ is an approximation of a sum of chemical concentration of saturates, aromatics, resins, and asphaltenes (SARA), or hexanes ($C_6$), or heptane plus ($C_{7+}$).

8. The method of claim 1, wherein the source is an external database, the method further comprising expanding the optical fluid database by merging data from a tool or sensor into the existing database.

9. The method of claim 1, wherein simulated visible (VIS), near infrared (NIR), and mid infrared (MIR) spectra includes a wavelength range from 450 nm to 3300 nm.

10. A method, comprising:
measuring a sample with an optical sensor to provide measurement data;
introducing the measurement data into a computer system;
applying at least one of a plurality of transformation models to simulate principal spectroscopy component (PSC) data using the measurement data;
ruggedizing the simulated PSC data by comparing at least one of a plurality of neural network ensemble (NNE) models and the at least one of the plurality of transformation models to produce an agreement, thereby producing a best estimated PSC data;
applying at least one of a plurality of NNE spectra reconstruction algorithms to simulate visible (VIS), near infrared (NIR), and mid infrared (MIR) spectra using the best estimated PSC data;
producing reconstructed field measurement data based on application of the at least one of the plurality of NNE spectra reconstruction algorithms; and
creating an empirical database to save the reconstructed field measurement data.

11. The method of claim 10, further comprising:
facilitating a wellbore operation based on the reconstructed field measurement data.

12. The method of claim 10, wherein the tool/sensor includes an optical sensor.

13. The method of claim 10, wherein the measurement data includes at least one of: carbon dioxide ($CO_2$), methane ($C_1$), ethane ($C_2$), propane ($C_3$), iso-butane ($iC_4$), n-butane ($nC_4$), iso-pentane ($iC_5$), n-pentane ($nC_5$), hexane plus ($C_{6+}$) where $C_{6+}$ is an approximation of a sum of chemical concentration of saturates, aromatics, resins, and asphaltenes (SARA), or hexanes ($C_6$), or heptane plus ($C_{7+}$).

14. The method of claim 10, wherein the reconstructed field measurement data is added to an existing database.

15. A method, comprising:
measuring a sample with an optical sensor to provide operational sensor measurement data;
introducing the operational sensor measurement data into a computer system;
converting, via the computer system, the operational sensor measurement data to PSC data via at least one of a plurality of neural network models;
constructing MIR fluid spectra with the PSC data using at least one of pre-determined PSC to MIR neural network models, the constructed MIR fluid spectra resulting in a MIR fingerprint;
estimating a dominant fluid type by comparing a degree of matching between the MIR fingerprint and spectra of reference oils and mud filtrates;
selecting nearest M oils by N filtrates reference data and simulate a mixed spectra at field temperature and pressure;
determining the degree of matching between the MIR fingerprint and simulated mixed spectra of M oils and N filtrates; and
formulating a degree of contamination based on the degree of matching between the MIR fingerprint and simulated mixed spectra of M oils and N filtrates.

16. The method of claim 15, further comprising:
comparing synthetic drilling fluid (SDF) model with the degree of contamination based on the MIR fingerprint, the simulated mixed spectra of M oils and N filtrates, and the PSC data.

17. The method of claim 15, further comprising:
evaluating MIR and SDF model prediction uncertainty by different PSC inputs and finalizing real-time model selection.

18. The method of claim 15, further comprising:
building a contamination time series curve as a function of volume of pumpout to estimate future point and end member values.

19. The method of claim 15, where M is any integer number between 1 and 10, and N is any integer number between 1 and 10.

20. The method of claim 15, wherein the determining the degree of matching between the MIR fingerprint and the simulated mixed spectra of M oils and N filtrates is repeated until the degree of contamination is stable within a desired tolerance of about 2%.

* * * * *